(12) United States Patent
Li et al.

(10) Patent No.: US 9,254,276 B2
(45) Date of Patent: Feb. 9, 2016

(54) LIPOSOME AND PERSONAL CARE COMPOSITION COMPRISING THEREOF

(75) Inventors: Chengwu Li, Beijing (CN); Naohisa Yoshimi, Botannia (SG); Xincheng Hu, Beijing (CN); Shuang Li, Beijing (CN); Yunhua Gao, Beijing (CN)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 13/357,916

(22) Filed: Jan. 25, 2012

(65) Prior Publication Data

US 2012/0189678 A1    Jul. 26, 2012

(30) Foreign Application Priority Data

Jan. 25, 2011    (WO) ................ PCT/CN2011/000111

(51) Int. Cl.

| | | |
|---|---|---|
| *A61K 9/127* | (2006.01) | |
| *A61K 31/19* | (2006.01) | |
| *A61K 31/198* | (2006.01) | |
| *A61K 31/203* | (2006.01) | |
| *A61K 31/215* | (2006.01) | |
| *A61K 31/375* | (2006.01) | |
| *A61K 31/704* | (2006.01) | |
| *A61K 8/14* | (2006.01) | |
| *A61K 8/55* | (2006.01) | |
| *A61K 8/60* | (2006.01) | |
| *A61K 8/67* | (2006.01) | |
| *A61K 8/92* | (2006.01) | |
| *A61P 17/00* | (2006.01) | |
| *A61Q 19/00* | (2006.01) | |
| *A61K 8/44* | (2006.01) | |
| *A61K 8/49* | (2006.01) | |
| *A61K 8/86* | (2006.01) | |
| *A61K 9/00* | (2006.01) | |
| *A61K 9/06* | (2006.01) | |

(52) U.S. Cl.
CPC . *A61K 31/19* (2013.01); *A61K 8/14* (2013.01); *A61K 8/44* (2013.01); *A61K 8/4946* (2013.01); *A61K 8/4993* (2013.01); *A61K 8/602* (2013.01); *A61K 8/86* (2013.01); *A61K 9/0014* (2013.01); *A61K 9/1271* (2013.01); *A61K 31/198* (2013.01); *A61K 31/203* (2013.01); *A61K 31/375* (2013.01); *A61K 31/704* (2013.01); *A61Q 19/00* (2013.01); *A61K 9/06* (2013.01); *A61K 2800/10* (2013.01); *A61K 2800/56* (2013.01)

(58) Field of Classification Search
CPC . A61K 9/1271; A61K 31/198; A61K 31/203; A61K 31/375; A61K 31/704; A61K 8/44; A61K 8/4993; A61K 8/86; A61K 8/14; A61K 9/0014; A61K 31/19; A61K 9/06; A61K 2800/10; A61K 2800/56; A61Q 19/00
See application file for complete search history.

(56) References Cited

U.S. PATENT DOCUMENTS

| | | | |
|---|---|---|---|
| 3,755,560 | A | 8/1973 | Dickert et al. |
| 4,421,769 | A | 12/1983 | Dixon et al. |
| 4,970,252 | A | 11/1990 | Sakuta et al. |
| 5,413,781 | A | 5/1995 | Giwa-Agbomeirele et al. |
| 5,569,464 | A | 10/1996 | Endo et al. |
| 5,654,362 | A | 8/1997 | Schulz, Jr. et al. |
| 5,686,082 | A | 11/1997 | N'Guyen |
| 5,725,845 | A | 3/1998 | Krog et al. |
| 5,760,116 | A | 6/1998 | Kilgour et al. |
| 6,015,568 | A | 1/2000 | Segot et al. |
| 6,174,533 | B1 * | 1/2001 | SaNogueira et al. ......... 424/401 |
| 6,391,863 | B1 | 5/2002 | Philippe et al. |
| 6,563,012 | B2 | 5/2003 | Hill |
| 6,872,401 | B2 | 3/2005 | Seyler et al. |
| 6,881,726 | B2 | 4/2005 | Chang et al. |
| D516,436 | S | 3/2006 | Campbell et al. |
| D535,191 | S | 1/2007 | Corker |
| D542,660 | S | 5/2007 | Thomas et al. |

(Continued)

FOREIGN PATENT DOCUMENTS

| | | |
|---|---|---|
| CN | 1762967 | 4/2006 |
| CN | 101366698 A | 2/2009 |

(Continued)

OTHER PUBLICATIONS

"Conjugate." Retrieved on Jun. 17, 2015. Retrieved from the internet<URL: http://chemistry.about.com/od/chemistryglossary/g/conjugatedefinition.htm>.*

(Continued)

*Primary Examiner* — Anoop Singh
*Assistant Examiner* — Doan Phan
(74) *Attorney, Agent, or Firm* — John G. Powell

(57) ABSTRACT

A liposome comprising a phospholipid, a hydrophobic active comprising a carboxylate group, and a component selected from a group consisting of: a hydrophilic adjuvant comprising a positively charged group, a complex of said hydrophobic active with said hydrophilic adjuvant, and combinations thereof. An aqueous liposome dispersion comprising the liposome, and a personal care composition comprising the liposome. A process of preparing the liposome, comprising the steps of: forming a premix by dissolving a phospholipid, a hydrophobic active comprising a carboxylate group in an organic solvent; evaporating off said organic solvent from the premix to form a phospholipid film; and hydrating said lipid film with a hydration medium comprising a hydrophilic adjuvant comprising a positively charged group and homogenize the medium to form an aqueous liposome dispersion.

14 Claims, 2 Drawing Sheets

(56) References Cited

U.S. PATENT DOCUMENTS

| | | | |
|---|---|---|---|
| D547,193 S | 7/2007 | Blasko et al. | |
| D547,661 S | 7/2007 | Blasko et al. | |
| 7,255,704 B2 | 8/2007 | Hogan et al. | |
| 7,297,668 B2 | 11/2007 | Johansson et al. | |
| D558,591 S | 1/2008 | Blasko et al. | |
| D563,221 S | 3/2008 | Ashiwa et al. | |
| D570,707 S | 6/2008 | Blasko et al. | |
| 7,811,342 B1 | 10/2010 | Hsu | |
| 7,947,097 B2 | 5/2011 | You | |
| 7,993,420 B2 | 8/2011 | Haerle et al. | |
| 8,038,751 B2 | 10/2011 | Starling | |
| 8,062,394 B2 | 11/2011 | Gaeta et al. | |
| 2003/0103916 A1* | 6/2003 | Imanaka et al. | 424/62 |
| 2004/0170586 A1 | 9/2004 | Ferrari et al. | |
| 2004/0175347 A1 | 9/2004 | Bissett | |
| 2006/0263309 A1 | 11/2006 | Bissett | |
| 2006/0275237 A1 | 12/2006 | Bissett et al. | |
| 2007/0028089 A1 | 2/2007 | Yukawa et al. | |
| 2007/0040306 A1 | 2/2007 | Morel et al. | |
| 2007/0172436 A1 | 7/2007 | Zhang | |
| 2007/0185038 A1 | 8/2007 | Bissett et al. | |
| 2007/0205226 A1 | 9/2007 | Honda et al. | |
| 2007/0264224 A1 | 11/2007 | Morris et al. | |
| 2007/0270472 A1* | 11/2007 | Beumer et al. | 514/351 |
| 2007/0281033 A1 | 12/2007 | Rochat | |
| 2008/0081052 A1 | 4/2008 | Zhang | |
| 2008/0154030 A1 | 6/2008 | Chang et al. | |
| 2008/0233183 A1 | 9/2008 | McCook | |
| 2008/0312304 A1 | 12/2008 | Zhang | |
| 2009/0017080 A1 | 1/2009 | Tanner et al. | |
| 2009/0098173 A1* | 4/2009 | Robinson et al. | 424/402 |
| 2010/0305169 A1* | 12/2010 | Robinson et al. | 514/358 |
| 2011/0162287 A1 | 7/2011 | Cai | |

FOREIGN PATENT DOCUMENTS

| | | | |
|---|---|---|---|
| EP | 1046393 A1 | 10/2000 | |
| JP | AS62042733 | 2/1987 | |
| JP | A2006137684 | 6/2006 | |
| KR | 9504697 B | 5/1993 | |
| WO | WO 01/01962 | 1/2001 | |
| WO | 03030860 A1 | 4/2003 | |
| WO | 2004024798 A1 | 3/2004 | |
| WO | 2005023208 A1 | 3/2005 | |
| WO | 2006102289 A2 | 9/2006 | |
| WO | 2006123324 A1 | 11/2006 | |
| WO | WO 2007039057 A1 * | 4/2007 | |
| WO | 2008087591 A1 | 7/2008 | |
| WO | WO 2009/105294 | 8/2009 | |
| WO | 2010077165 A1 | 7/2010 | |
| WO | 2010140869 A2 | 12/2010 | |

OTHER PUBLICATIONS

"Complex." Retrieved on Jun. 17, 2015. Retrieved from the internet <URL: http://www.britannica.com/science/complex-in-chemistry>.*

Bissett, D.L., et al. "Niacinamide: A B Vitamin that Improves Aging Facial Skin Appearance"; Dermatol Surg Jul. 31, 2005; 12 pages.

Draelos. Z.D., "Clinical Situations Conducive to Proactive Skin Health and Anti-Aging Improvement"; J Investig Dermatol Symp Proc; Apr. 13, 2008(1): 25-7.

International Search Report; PCT/CN2011/000111; International Filing Date Jan. 25, 2011; 12 pages.

Marjukka, S.T. "Chemical Enhancement of Percutaneous Absorption in Relation to Stratum Corneum Structural Alterations"; J. Control Release, May 20, 1999; 59(2); 149-61.

Osborne Osborne, David, "Skin Penetration Enhancers Cited in the Technical Literature, Pharmaceutical Technology", 1997, pp. 58-66.

Pathan, "Chemical Penetration Enhancers for Transdermal Drug Delivery Systems", Tropical Journal of Pharmaceutical Research, vol. 8(2), pp. 173-179 (2009).

Williams et al., "Penetration Enhancers", Advanced Drug Delivery Reviews 56, pp. 603-618, 2004.

European Extended Search Report; App. No. 11 857 221.3; Jul. 17, 2014; 5 pages.

Katahira N et al "Enhancement of topical delivery of a lipophilic drug from charged multilamellar liposomes.", Journal of Drug Targeting 1999, vol. 6, No. 6, 1999, pp. 405-414.

Benson Heather A E: "Elastic Liposomes for Topical and Transdermal Drug Delivery", Current Drug Delivery, vol. 6, No. 3, Jul. 2009, pp. 217-226.

Trotta M et al: "Elastic Liposomes for Skin Delivery of Dipotassium Glycyrrhizinate", International Journal of Pharmaceutics, Elsevier BV, NL, vol. 241, No. 2, Jul. 25, 2002, pp. 319-327.

Li S et al: "A novel transdermal fomulation of 18[betaj-glycyrrhetic acid with lysine for improving bioavailability and efficacy", Jan. 1, 2012, vol. 25, No. 5, Jan. 1, 2012, pp. 257-268.

Chen J et al: "Skin permeation behavior of elastic liposomes: Role of formulation ingredients", Expert Opinion on Drug Delivery 2013 Informa Healthcare GBR, vol. 10, No. 6, Jun. 2013, pp. 845-856.

* cited by examiner

LIPOSOME AND PERSONAL CARE COMPOSITION COMPRISING THEREOF

CROSS REFERENCE TO RELATED APPLICATIONS

This application claims the benefit of PCT China Application No. PCT/CN2011/000111, filed Jan. 25, 2011.

FIELD OF THE INVENTION

The present invention relates to a liposome which provides improved delivery of hydrophobic actives into skin, relates to aqueous liposome dispersion, relates to a personal care composition comprising the liposome, and relates to a method of preparation the liposome.

BACKGROUND OF THE INVENTION

In a cosmetic application, the topical delivery of skin actives into a deep skin layer, i.e., across the stratum corneum to the dermal layer, is oftentimes desired. However, an intact skin poses a major obstacle to the delivery of skin actives through the stratum corneum. The stratum corneum consists of corneocytes embedded in a lipid matrix composed of organized lipid bi-layers, where the lipid materials act as extra intercellular glue sealing the spaces between the cells in the stratum corneum.

In order to deliver skin actives across the intact skin, several approaches have been developed. One of them is to either destroy or fluidize the lipid bi-layer in the stratum corneum using hydrophobic medium such as the oil phase in an emulsion, thereby enhancing the penetration of actives.

Another approach is the use of a vesicular system such as liposomes. Liposomes are vesicles composed of phospholipid bi-layers. A phospholipid molecule has a polar "head" and two non-polar "tails". Due to its structure, the phospholipid tends to form a vesicular bi-layer, i.e. liposome, with the polar heads of phospholipids aligning toward an outer or inner aqueous phase while the non-polar tails align toward each other. Such liposomes have been used to construct carriers for the delivery of actives.

However, effective entrapment of actives into a liposome and maintaining the stability of such a liposome may still be a challenge. It is known in the industry that the chemistry of to-be-entrapped actives affects the entrapment efficiency and associated loading rate of the actives into liposome. Hydrophobic actives comprising a carboxylate group, like glycyrrhetinic acid, pose such a challenge.

Therefore, there exists a need for a liposome into which hydrophobic actives comprising a carboxylate group may be formulated. The liposome should be stable and have a satisfying loading rate of such hydrophobic actives, and thereby have improved penetration into deep skin layer, and thus have improved residual amount of actives within skin layers.

While many others have sought to improve the liposome delivery of hydrophobic actives, the benefit of this present invention was not met and not disclosed in the art. See, for example, U.S. Pat. No. 5,569,464 relating to an aqueous dispersion for encapsulating hydrophilic or hydrophobic drugs, where the aqueous dispersion comprises a liposome, a hydroxyl acid, and an amino acid as a stabilizing agent, and EP patent 0211647 B1 relating to a liposome-forming composition comprising a hydrating agent and liposome-forming materials.

SUMMARY OF THE INVENTION

The present invention relates to a liposome comprising a) a phospholipid, b) a hydrophobic active comprising a carboxylate group, and c) a component selected from a group consisting of: a hydrophilic adjuvant comprising a positively charged group, a complex of said hydrophobic active with said hydrophilic adjuvant, and combinations thereof. The present invention also relates to an aqueous liposome dispersion, and relates to a personal care composition comprising the liposome. The present invention also relates to a process of preparing the present liposome, the process comprising the steps of: forming a premix by dissolving a phospholipid and a hydrophobic active comprising a carboxylate group in an organic solvent; evaporating off said organic solvent from said premix to form a phospholipid film; hydrating said film with a hydration medium comprising a hydrophilic adjuvant comprising a positively charged group, and homogenizing the hydration medium to form an aqueous liposome dispersion.

DETAILED DESCRIPTION OF THE INVENTION

Figure 1:
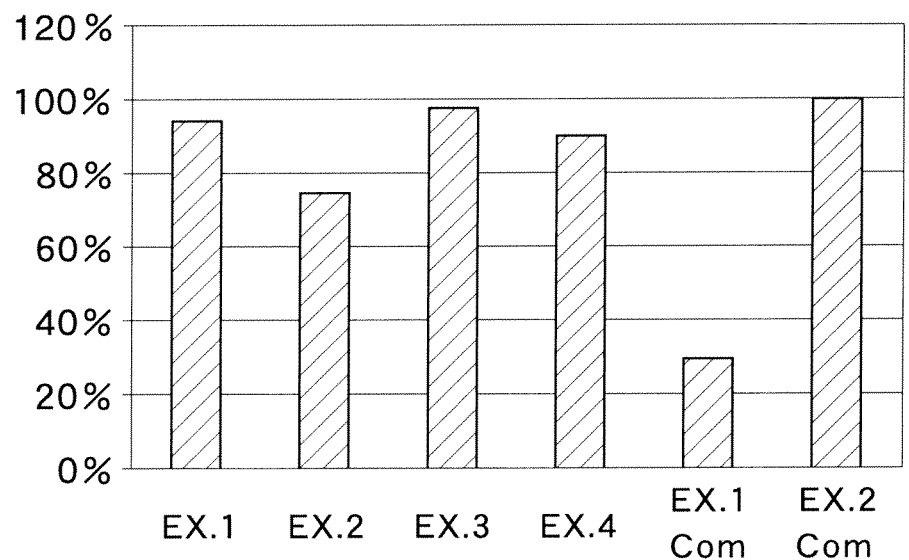
FIG. 1 shows the comparison of the loading rates for Examples 1-4 and comparative Example 1 liposome, and comparative Example 2 cream.

While the specification concludes with claims particularly pointing out and distinctly claiming the invention, it is believed that the present invention will be better understood from the following description.

All percentages, parts and ratios are based upon the total weight of the aqueous liposome dispersion, unless otherwise specified. All such weights as they pertain to listed ingredients are based on the active amount and, therefore, do not include carriers or by-products that may be included in commercially available materials.

All ingredients such as actives and other ingredients useful herein may be categorized or described by their cosmetic and/or therapeutic benefit or their postulated mode of action. However, it is to be understood that the active and other ingredients useful herein may, in some instances, provide more than one cosmetic and/or therapeutic benefit or operate via more than one mode of action. Therefore, classifications herein are made for the sake of convenience and are not intended to limit an ingredient to the particularly stated application or applications listed.

As used herein, "liposome" is used to describe oligo-lamellar lipid vesicles comprising one or more natural or synthetic lipid bi-layers surrounding an internal aqueous phase.

As used herein, "hydrophobic active" means the active has a Log value of its octanol/water partition coefficient index of greater than zero, preferably from 0-8, more preferably from 1-7. The hydrophobic active comprises a dissociable carboxylate group at the pH when it is formulated into a liposome, which means the carboxylate group can be carboxylic acid group or salts thereof.

As used herein, "hydrophilic adjuvant" means the adjuvant has a Log value of the octanol/water partition coefficient index of less than zero.

As used herein, "positively charged group" means the hydrophilic adjuvant comprises a group which bears a positive charge under the pH condition of the present aqueous liposome dispersion, for example at pH 7.0.

As used herein, "elastic liposome" means the liposome tends to undergo a shape change when penetrating through the skin harrier.

The present invention relates to a liposome comprising a phospholipid, a hydrophobic active comprising a carboxylate group, and a hydrophilic adjuvant comprising a positively charged group. The present liposome may be prepared in the form of aqueous liposome dispersion. The present liposome may also be incorporated into a personal care composition selected from a group consisting of creams, emulsions, gels, lotions, clear lotions, and combinations thereof.

Phospholipid

The present liposome comprises a phospholipid. The phospholipid may be selected from a group consisting of a natural phospholipid, a synthetic phospholipid, and combinations thereof. Lecithin is one of the natural resources for phospholipid. Lecithin is a mixture found in egg yolk and soy et. al. It comprises a number of phospholipids including phosphatidylcholine (PC), phosphatidylethanolamine (PE), and phosphatidylinositol (PI). Natural phospholipids also include, e.g. hydrogenated soy PC (HSPC), sphingomyelin, and phosphatidylglycerol (PG).

Synthetic phospholipids include, but are not limited to, derivatives of phosphocholine (for example, DDPC, DLPC, DMPC, DPPC, DSPC, DOPC, POPC, DEPC), derivatives of phosphoglycerol (for example, DMPG, DPPG, DSPG, POPG), derivatives of phosphatidic acid (for example, DMPA, DPPA, DSPA), derivatives of phosphoethanolamine (for example, DMPE, DPPE, DSPE DOPE), derivatives of phosphoserine (for example, DOPS), PEG derivatives of phospholipid (for example, mPEG-phospholipid, polyglycerin-phospholipid, functionalized-phospholipid, and terminal activated-phospholipid). The chemical name of the phospholipid derivatives corresponding to the abbreviations mentioned above can be found in the web page of http://en.wikipedia.org/wiki/Phospholipid.

In one embodiment of the present invention, the phospholipid is a hydrogenated phospholipid, specifically, a hydrogenated soy PC (HSPC).

The liposome comprises from about 1%, 3% or 6% to about 8%, 10% or 20% of phospholipid by weight of the aqueous liposome dispersion.

The present liposome may optionally include a steroid. Steroid can help increase the stability of the lipid bi-layer and decreases the leakage problem of the liposome.

Hydrophobic Active

The present liposome comprises a hydrophobic active comprising a carboxylate group.

In one embodiment, the hydrophobic active comprises in addition to the carboxylate group, a hydrophobic domain comprising at least one aryl group. In one embodiment, the hydrophobic domain comprises multi-aryl group. Preferably, the aryl group and the carboxylate group at located at two opposing ends of the hydrophobic active. Exemplary hydrophobic actives are selected from a group consisting of glycyrrhetinic acid (GA), glycyrrhetinyl stearate, glycyrrhizinic acid undecylenoyl phenylalanine (trade name Sepiwhite™), retinoic acid, and combinations thereof.

Glycyrrhetinic acid is an active provides a whitening benefit. As shown below, its structural formula includes at one end a hydrophobic multi-aryl group and at the other end a hydrophilic carboxylate group.

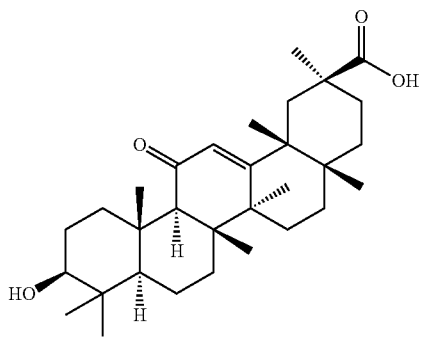

Undecylenoyl phenylalanine, which is a modified phenylalanine, has the structural formula shown below. It includes a hydrophobic aryl group at one end, and a hydrophilic carboxylate group at the other end.

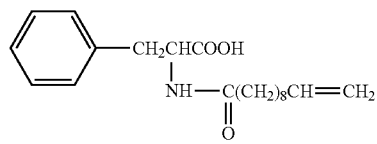

Suitable hydrophobic actives may include those used in the cosmetic industry and/or in pharmaceutical industry.

The hydrophobic active can present in the present liposome in an amount of from about 0.01%, 0.05%, 0.1%, 0.3%, 0.6% or 0.9% to about 1.2%, 1.5% or 5% by weight of the aqueous liposome dispersion. Alternatively, the amount of hydrophobic active can also be based on the amount of phospholipid used in constructing the liposome, usually in an amount of from about 1% to about 20% by weight of the phospholipid.

Hydrophilic Adjuvant

The liposome comprises a hydrophilic adjuvant comprising a positively charged group. The positively charged group is able to interact with the carboxylate group of the hydrophobic active to form a complex. The positively charged group is preferably a positively charged ammonium group ($-NH_3^+$). In one embodiment, the hydrophilic adjuvant of present liposome comprises at one end a positively charged group, and comprises at the other end which is opposes the positively charged end, a carboxylate group. In another embodiment of the present invention, the hydrophilic adjuvant is selected from a group consisting of lysine (formula I), arginine (formula II), histidine (formula III), and combinations thereof.

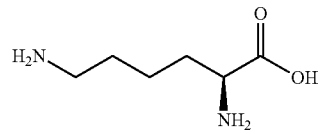

I

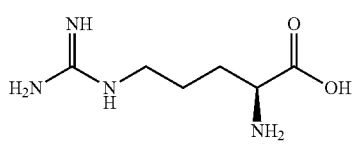

II

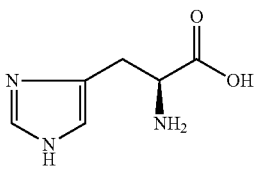

It is believed that the positively charged group of the hydrophilic adjuvant complexes with the carboxylate group of the hydrophobic active. The un-complexed ends of the hydrophilic adjuvant and the aryl end hydrophobic active make the formed complex amphoteric in nature. For example, the structure of the complex formed by glycyrrhetinic acid and lysine is shown below in formula IV.

Without being bound by theory, the amphoteric complex formed by hydrophilic adjuvant and the hydrophobic active is believed to help maintain a stable insertion of itself among the phospholipids in the bi-layer wall of the liposome and possibly further influencing the elasticity of the liposome. An improved loading rate, accordingly an improved penetration and residual amount of hydrophobic actives into the skin layer, can be achieved through the present liposome.

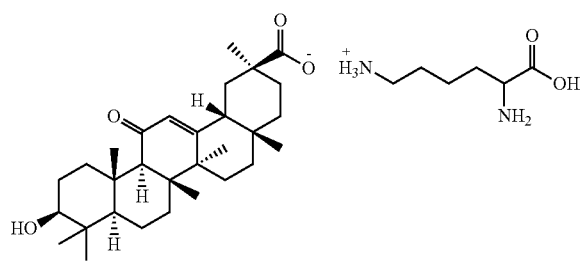

The hydrophilic adjuvant is present in the present liposome in an amount of from about 0.05%, 0.3%, 0.8% or 1% to about 1.5%, 2%, 8% or 10% by weight of the aqueous liposome dispersion.

Alternatively, the amount of hydrophilic adjuvant can also be based on the amount of phospholipid used in constructing the liposome, usually from about 1% to about 20% by weight of the phospholipid. The molar ratio of the hydrophilic adjuvant to the hydrophobic active is from about 1/10, 1/4, 1/2 or 1 to about 2, 4 or 10.

Elasticity Enhancer

The liposome of the present invention is preferably an elastic liposome comprising an elasticity enhancer. The elasticity enhancer may be selected from a group consisting of sodium cholate, sodium deoxycholate, polysorbate 80 (Tween 80), sorbitan monooleate (Span 80), oleic acid, dipotassium glycyrrhizinate (KG) and cholesteryl ether, and combinations thereof. In one embodiment, the elasticity enhancer is a surfactant, e.g., an anionic surfactant, a non-ionic surfactant or a zwitterionic surfactant, preferably a non-ionic surfactant. Preferably, the non-ionic surfactant is Tween 80, Span-80 and/or polyoxyethylene cholesteryl ether with formula $C_{27}H_{45}O(CH_2CH_2O)_nH$, wherein n is from 5 to 15, for example 5, 10 or 15.

In the present invention, the elasticity enhancer is present in an amount of from about 0.01%, 0.1% or 0.4% to about 2.5% or 10% by weight of the aqueous liposome dispersion.

Other Ingredients

The present liposome may optionally comprise from about 0.01% or 0.1% to about 2% or 5% of an antioxidant by weight of the aqueous liposome dispersion. The antioxidant may be selected from a group consisting of vitamin E, vitamin E ester, vitamin C, vitamin C ester and a combination thereof. In a preferred embodiment, the liposome comprises vitamin E acetate.

Method of Preparation

The present liposome may be prepared as an aqueous liposome dispersion following steps described below. First, form a premix by completely dissolving all hydrophobic materials including the phospholipid and the hydrophobic active in an appropriate organic solvent which is acceptable for the liposome preparation in the cosmetic and pharmaceutical industry, e.g., ethanol, at 70° C. in a vessel. Trace amount of solvent can be removed under vacuum overnight at room temperature. The organic solvent is then removed from the premix, e.g., through rotary vacuum evaporation. Then, a deposited phospholipid film is formed at the bottom of the vessel after the removal of the solvent. An aqueous medium, e.g., a phosphate buffer solution (PBS), comprising the hydrophilic adjuvant, is used to hydrate the film. After hydration, the aqueous medium is homogenized to form aqueous liposome dispersion. The homogenization can be achieved through constant agitation followed by supersonification or through a commercially available homogenizer, e.g., Emulsiflex C5 from Avestin, Canada. The choice of hydration medium, the manner of hydration and homogenization used to form a liposome is commonly known in the art. The aqueous liposome dispersion is formed and can be stored at room temperature.

Method of Measurement

Loading Rate

The loading rate is used to measure the percentage of the hydrophobic active successfully encapsulated into the liposome against the total amount of the hydrophobic active that is originally fed into the organic solvent for preparing the aqueous liposome dispersion. Loading rate is calculated as the entrapment efficiency (EE %)=$C_S/C_U \times 100\%$.

$C_S$ represents the amount of hydrophobic active loaded into the liposome. It is measured by first removing the unloaded hydrophobic active from the aqueous liposome dispersion, and then disrupting the structure of the liposome using pure ethanol to release the hydrophobic active for concentration measuring. Specifically, one aliquot (0.2 ml) of the final preparation of the aqueous liposome dispersion is dialyzed against an appropriate aqueous medium, for example 500 ml PBS, to completely remove any unloaded hydrophobic active. After dialysis, the remaining contents in the dialysis bag is removed and transferred to a separate vessel, and ethanol is added into that vessel to reach a final volume of 25 ml. The concentration of loaded hydrophobic actives ($C_S$) in ethanol is then determined by HPLC, and amount of hydrophobic active is calculated accordingly.

$C_U$ represents the total amount of hydrophobic active originally fed into the organic solvent for preparing the aqueous liposome dispersion. It includes both the amount of the hydrophobic active loaded into liposome and the amount of active presented as unloaded chemical in the aqueous phase of the liposome dispersion. Specifically, same aliquot (0.2 ml) of the preparation of the aqueous liposome dispersion is transferred to a separate vessel, and ethanol is added to that vessel to reach a final volume of 25 ml. The concentration of total amount of hydrophobic active ($C_U$) is then determined by HPLC, and amount of hydrophobic active is calculated accordingly.

In the HPLC measurement, a HPLC equipment coded LC-2010AHT from Shimadza Corporation, Kyoto, Japan can be used together with a chromatography column of Hypersil ODS (250 mm*4.6 mm) from Thermo Fisher Scientific, and a mobile phase of methanol:water=95:5 with pH adjusted to 3.5 by H3PO4 in the chromatography. Although HPLC is used as suitable method of measuring the concentration of hydrophobic active, other concentration measurement method can be used as well.

Penetration Efficiency Measurement—Diffusion Cell Test

Penetration efficiency is used to measure the amount of hydrophobic active that penetrates through a certain surface area of the skin and reach the dermal layer. A Franz diffusion cell system, also called, Franz-Diffusion chamber, is commonly used in the industry for measuring the skin penetration efficiency of an active.

The Franz-Diffusion chamber comprises a donor compartment at a upper end and an acceptor compartment at an lower end, where the inner space of the two compartments are separated by a barrier. The acceptor compartment normally has a sampling port for the convenience of a real-time monitoring and analyzing of the sample drained through the barrier to reach the acceptor compartment. The barrier may be a natural skin preparation, or artificial skin constructs (ASC). An ASC can be cultivated from different cell types and comprises a dermis and an epidermis equivalent.

During test, a sample is loaded into the donor compartment and is set to drain through the barrier toward the acceptor compartment. The acceptor compartment is filled with 15% v/v ethanol-PBS solution. Samples can be taken out from the sampling port of the acceptor compartment for measuring. The penetration efficiency is calculated as the amount of the skin active that reach the acceptor compartment divided by the surface area of the barrier.

Residual Amount of Hydrophobic Actives within Skin Layers

This residual amount is used to measure the total amount of active remained in the skin, across all the depth of its penetration in the skin. At the end of the penetration test described above, when all the sample in the donor compartment has drained through the barrier, the barrier is removed and rinsed on its surface with pure water for five times before being put back to the Franz-Diffusion chamber. Then receptor compartment is filled with 50% v/v ethanol-PBS and the Franz Diffusion Chamber if left standing for a further 12 hours in order to dissolve all the GA remained in various layers of the barrier. Then sample can be drawn out from the sampling port of receptor compartment and the concentration of actives in the sample can be determined by HPLC.

Method of Use

The present liposome may be incorporated into a personal care composition, including a cosmetic composition and a pharmaceutical composition for the purpose of improved transdermal delivery of a hydrophobic active. The cosmetic composition may be in the form of a cream, an emulsion, a gel, a lotion, a clear lotion, and combinations thereof.

EXAMPLES

Examples 1-4 relate to the aqueous liposome dispersions of the present invention. Example 1 relates to a normal liposome, Example 2 relates liposome further incorporating cholesterol, Examples 3 and 4 related to liposomes further incorporating elasticity enhancers. Comparative examples 1-2 illustrate those compositions comprising a hydrophobic active, but are outside the scope of the present invention. Specifically, comparative example 1 relates to a liposome deficient of the hydrophilic adjuvant, and comparative example 2 shows an oil-in-water cream as a vehicle for hydrophobic active delivery, as compared to the liposome delivery.

The examples are given solely for the purpose of illustration and are not to be construed as limitations of the present invention, as many variations thereof are possible without departing from the spirit and scope of the invention. Where applicable, ingredients are identified by chemical or CTFA name, or otherwise defined below.

TABLE 1

|   | | Example 1 | Example 2 | Example 3 | Example 4 | Comparative Example 1 | Comparative Example 2 |
|---|---|---|---|---|---|---|---|
| 1 | hydrogenated soy phosphocholine[1] | 3% | 3% | 3% | 3% | 3% | |
| 2 | vitamin E acetate | 0.72% | 0.72% | 0.72% | 0.72% | 0.72% | |
| 3 | cholesterol | | 0.55% | | | | |
| 4 | Tween 80 | | | 0.55% | 0.275% | 0.55% | |
| 5 | Polyoxyethylene (10) cholesteryl ether[2] | | | | 0.275% | | |
| 6 | glycyrrhetinic acid[3] | 0.30% | 0.30% | 0.30% | 0.30% | 0.20% | 0.30% |
| 7 | L-lysine[4] | 0.21% | 0.21% | 0.21% | 0.21% | | |
| 8 | oil-in-water cream base | | | | | | 99.7% |
|   | Loading rate of hydrophobic active | 94.3% | 75.0% | 98.0% | 90.3% | 30.5% | 100% |

[1]Hydrogenated soy phosphocholine (HSPC), commercially available under the name Phopholipon 80H from Shanghai Toshisun Enterprises Co. Ltd
[2]Polyoxyethylene (10) cholesteryl ether, from Nihon Emulsion Co. Ltd
[3]glycyrrhetinic acid, from Xinjiang Tianshan Pharmaceutical Ltd.
[4]L-lysine, Biotech grade, from Solarbio Science & Technology Co., Ltd The Example 1 liposome is prepared by first forming a premix by dissolving 1.2 gram of hydrogenated soy phosphocholine (HSPC), 0.288 g vitamin E acetate and 120 mg glycyrrhetinic acid (GA) in 20 ml ethanol in a clean round bottom flask at 70° C. Ethanol is then removed through rotary vacuum evaporation and a lipid film is formed on the bottom of the flask. The lipid film is then hydrated with 40 g 0.005 M, pH 7.0 PBS solution comprising 82 mg dissolved L-lysine, accompanying magnetic agitation for 30 min. The molar ratio of GA:Lysine=1:2. The hydration solution then goes through a high-pressure homogenization using a homogenizer available under the name Emulsiflex C5 from Avestin, Canada for 3 times at 5000 psi to get homogenous aqueous liposome dispersion. The resultant sample is stored at room temperature.

The preparation of the three liposomes of Example 2-4 differs from the preparation of Example 1 liposome in further addition of 219.9 mg of cholesterol, 219.9 mg of Tween-80, a mixture of 110 g Tween-80 and 110 g polyoxyethylene cholesteryl ether of formula $C_{27}H_{45}O(CH_2CH_2O)_{10}H$ (also named CS10), respectively, into the ethanol premix.

The preparation of Comparative Example 1 liposome differs from the preparation of Example 3 liposome in that the hydration medium is deficient of lysine, and a slightly lower level of glycyrrhetinic acid level is added.

The preparation of Comparative Example 2 composition can be conducted through a conventional method for preparing an oil-in-water emulsion. The Example 2 cream comprises 0.3% glycyrrhetinic acid, and 99.7% oil-in-water cream base comprising 1.4% of fatty alcohols (a mixture of cetyl alcohol, stearyl alcohol, behenyl alcohol and cetearyl alcohol), 2% of silicone oil (dimethicone and dimethiconol), 0.25% silicone powder (polymethylsilsesquioxane) and 2% Sepigel 305, water is added along with other ingredients to reach total amount of 100%.

Measurement and Efficacy

1. Loading Rate Measurement

The loading rates of the present Examples 1-4 liposomes and comparative Example 1 liposome are measured following the measurement method described in above METHOD OF MEASUREMENT section. The glycyrrhetinic acid loading rate in the comparative example 2 cream is regarded as 100%, since it is completely incorporated in the oil phase of the cream.

It can be seen from above Table 1 that the present liposome of Examples 1-4 comprising lysine has a significantly higher loading rate than that of comparative Example 1 liposome which does not comprise lysine. The loading rate data is also drawn into a graph in FIG. 1.

2. Penetration Efficiency Measurement

The Franz Diffusion Chamber is equilibrated with pure water for 1 hour before samples are added into the donor compartment. A rat skin preparation of a suitable surface area corresponding to the effective diffusion area of the Franz diffusion chamber is used as the barrier placed between receptor and donor compartment. The Franz diffusion chamber having an effective diffusion area of 0.66 $cm^2$ and receiver cell volume of 2.5 ml is used for this measurement.

An aliquot of 200 µl of the aqueous liposome dispersion preparation is transferred into the donor compartment, and the experiment is conducted with the donor compartment non-occluded. The receptor compartment is filled with 15% v/v of ethanol-PBS (pH=7.4) solution. The ethanol-PBS solution in the receptor cells are constantly homogenized using a magnetic mixer at a speed of 280 rpm at 37±0.2° C. 2.5 ml of samples from the receptor compartment are withdrawn at 1, 3, 5, 8 h and glycyrrhetinic acid concentrations are determined by HPLC, and amount of the penetrated GC is calculated accordingly by multiplying with the sample volume.

TABLE 2

Comparison of GA penetration efficiency

| Time (hr) | Example 3 (µg/$cm^2$) | Comparative Ex. 2 (µg/$cm^2$) |
|---|---|---|
| 0 | 0 | 0 |
| 1 | 0 | 0 |
| 3 | 0.1206 ± 0.0471 | 0.0217 ± 0.0433 |
| 5 | 0.9754 ± 0.2741 | 0.3610 ± 0.3124 |
| 8 | 3.5375 ± 0.9729 | 1.5765 ± 0.7410 |

Figure 2:
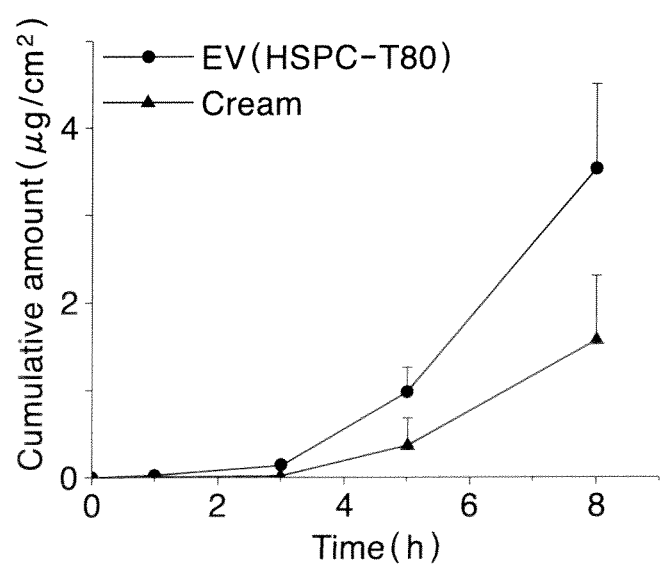
FIG. 2 shows the comparison of Example 3 liposome and comparative Example 2 cream in terms of GA penetration through rat skin within 8 hours.

It can be seen from Table 2 that the amount of glycyrrhetinic acid penetrated through rat skin is significantly increased when delivered via the present liposome of Examples 3, as compared to the delivery through the oil-in-water cream of comparative Example 2. This GA penetration efficiency data is also drawn into a graph shown in FIG. 2.

3. Residual Measurement

At the end of the penetration test when all the samples in the donor compartment has drained through the rat skin, the skin is taken out for residual measurement following the method described in previous METHOD OF MEASUREMENT section.

TABLE 3

Comparison of GA residue amount

|  | GA residual amount (µg/$cm^2$) |
|---|---|
| Example 3 | 6.5933 ± 0.9198 |
| Comparative Ex. 2 | 1.7348 ± 1.1049 |

Figure 3:
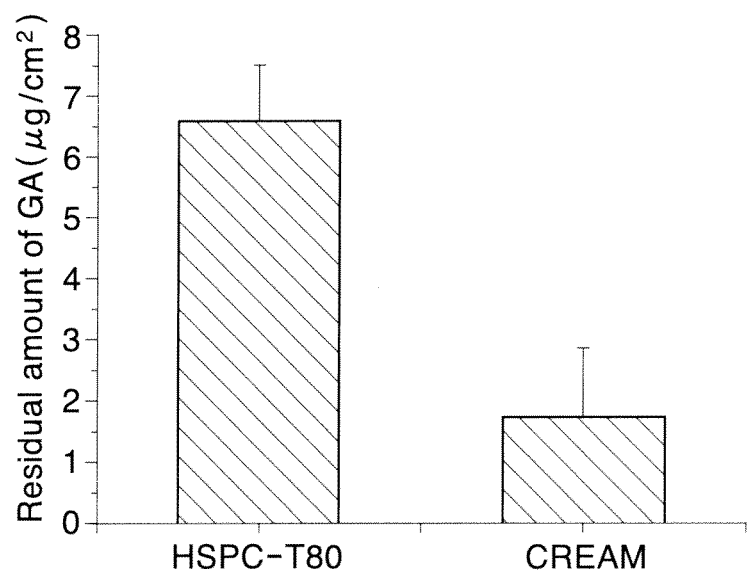
FIG. 3 shows the comparison of Example 3 liposome and comparative Example 2 cream in terms of GA residual amount in the rat skin after 8 h of penetration.

It an be seen from Table 3 that the amount of glycyrrhetinic acid accumulated across all layers of the rat skin are significantly improved delivery via Example 3 liposome, as compared to the delivery via glycyrrhetinic acid through an oil-in-water cream of comparative Example 2. This Residual Measurement data is also drawn into a graph shown in FIG. 3.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A liposome comprising:
   a) a phospholipid;
   b) a hydrophobic active selected from the group consisting of glycyrrhetinic acid, glycyrrhetinyl stearate, glycyrrhizinic acid, undecylenoyl phenylalanine, ascorbyl tetraisopalmitate, and combinations thereof; and
   c) a hydrophilic adjuvant comprising a positively charged group, wherein the hydrophilic adjuvant ionically bonds with the hydrophobic active to form a complex with said hydrophobic active and wherein the molar ratio of said hydrophobic active to said hydrophilic adjuvant is from about 1:10 to about 10:1.

2. The liposome of claim 1 wherein said hydrophilic adjuvant is a basic amino acid selected from the group consisting of lysine, arginine, histidine and combinations thereof.

3. The liposome of claim 1 wherein said hydrophobic active is present in an amount of from about 1% to about 20% by weight of the phospholipid.

4. The liposome of claim 1 wherein said hydrophilic adjuvant is present in an amount of from about 1% to about 20% by weight of the phospholipid.

5. The liposome of claim 1 wherein said phospholid is a hydrogenated phospholipid.

6. The liposome of claim 1 further comprising an elasticity enhancer selection from the group consisting of a nonionic surfactant, polyoxyethylene cholesteryl ether, and combinations thereof.

7. The liposome of claim 6 wherein said nonionic surfactant is polysorbate 80 or sorbitan monooleate.

8. The liposome of claim 6 wherein said polyoxyethylene cholesteryl ether is $C_{27}H_{45}O(CH_2CH_2O)_nH$, wherein n is from 5 to 15.

9. The liposome of claim 1 further comprising an antioxidant selected from the group consisting of vitamin E, vitamin E ester, vitamin C, vitamin C ester and combinations thereof.

10. An aqueous liposome dispersion comprising the liposome of claim 1, wherein the phospholipid is present in an amount of from about 1% to about 20% by weight of said aqueous solution.

11. The aqueous liposome dispersion of claim 10, wherein an elasticity enhancer is present in an amount of from about 0.01% to about 10% by weight of said aqueous dispersion.

12. The aqueous liposome dispersion of claim 10, wherein the antioxidant is present in an amount of from about 0.01% to about 5% by weight of said aqueous dispersion.

13. A personal care composition comprising the liposome of claim 1, said personal care composition is in a form selected from the group consisting of creams, emulsions, gels, lotions, clear lotions, and combinations thereof.

14. A personal care composition made by using the aqueous liposome of claim 10, said personal care composition is in a form selected from the group consisting of creams, emulsions, gels, lotions, clear lotions, and combinations thereof.

* * * * *